US00PP09260P

United States Patent [19]

Aharoni

[11] Patent Number: Plant 9,260

[45] Date of Patent: Aug. 22, 1995

[54] FERN PLANT NAMED DELILA

[75] Inventor: Miriam Aharoni, Kibbutz Yifat, Israel

[73] Assignee: Milestone Agriculture Inc., Apopka, Fla.

[21] Appl. No.: 257,101

[22] Filed: Jun. 7, 1994

[51] Int. Cl.[6] ..... A01H 5/00
[52] U.S. Cl. ..... Plt./88.3
[58] Field of Search ..... Plt. 88.3

[56] References Cited

U.S. PATENT DOCUMENTS

P.P. 5,755 6/1986 Mills et al. ..... Plt./88.3

*Primary Examiner*—James R. Feyrer

[57] ABSTRACT

A distinct cultivar of Fern plant named Delila, characterized by its symmetrical and spherical plant habit; arching to pendent fronds that cover the container; numerous fronds that form a dense plant canopy; short and broad fronds and pinnae; deeply crenate pinnae margins; and slightly curved pinnae that are undulated from base to tip giving a wavy, not flat, appearance.

2 Drawing Sheets

The present invention relates to a new and distinctive cultivar of Fern, botanically known as *Nephrolepis exaltata,* and hereinafter referred to by the cultivar name Delila.

The new cultivar was discovered by me at Biological Industries Co. Ltd., Kibbutz Beit Haemek, Israel, as a naturally occurring sport or mutation of the *Nephrolepis exaltata* cultivar Welch.

Asexual reproduction of the new cultivar by tissue culture propagation at Biological Industries Co. Ltd., Kibbutz Beit Haemek, Israel, has shown that the unique features of this new Fern are firmly fixed and retained through successive generations of asexual reproduction.

The cultivar Delila has not been observed under all possible environmental conditions. The phenotype may vary significantly with variations in environment such as temperature and light intensity. The following observations, measurements and comparisons describe plants grown in Apopka, Fla., under conditions which closely approximate those generally used in commercial practice.

The following traits have been repeatedly observed and are determined to be the distinctive and unique characteristics of Delila. These characteristics in combination distinguish Delila as a new and distinct cultivar:

1. Symmetrical and spherical plant shape that is appropriate for having basket containers.
2. Arching to pendent fronds that cover the container.
3. Numerous fronds that form a dense plant canopy.
4. Fronds that are short and broad.
5. Pinnae that are short and broad.
6. Pinnae margins that are deeply crenate.
7. Pinnae that are slightly curved inward towards the midvein and undulated from base to tip giving a wavy, not flat, appearance.

Delila differs from its parent cultivar, *Neophrolepis exaltata* cultivar Welch in its denser and more compact plant habit, more curved fronds, more spherical appearance, and less occurrence of dieback of fronds in the center of the plant.

The new cultivar is most similar to the *Neophrolepis exaltata* cultivar Dallas Jewel, disclosed in U.S. Plant Pat. No. 5,755, in its similar pinnae color and plant vigor. Delila differs from Dallas Jewel in the following characteristics:

1. Plant shape of Delila plants is symmetrical and spherical compared to upright, loose and nonsymmetrical plant shape of Dallas Jewel plants.
2. Fronds of Delila plants are arching to pendent. Fronds of Dallas Jewel plants are erect to slightly arching.
3. Plants of Delila are shorter and wider than plants of Dallas Jewel.
4. Fronds of Delila plants are shorter and slightly broader than fronds of Dallas Jewel plants.
5. The rachis length of fronds of Delila plants is shorter than the rachis length of fronds of Dallas Jewel plants.
6. Delila plants have more fronds per plant than plants of Dallas Jewel.
7. Fronds of Delila plants have fewer pinnae per frond compared to fronds of Dallas Jewel plants.
8. Pinnae of Delila plants are broader than pinnae of Dallas Jewel plants.
9. The pinnae margin of Delila plants is more deeply crenate compared to pinnae margin of Dallas Jewel plants.
10. Pinnae of Delila plants have fewer lobes than pinnae of Dallas Jewel plants.
11. Pinnae of Delila plants are slightly curved inward towards the midvein and undulated from the pinnae base to tip giving a wavy, not flat, appearance. Pinnae of Dallas Jewel plants are flat or slightly curved inward towards the midvein.
12. In general appearance, plants of Delila appear softer and more feathery than Dallas Jewel plants.

A detailed comparison of Delila and Dallas Jewel plants appears in Chart A at the end of the specification.

The accompanying colored photographs illustrate the overall appearance of the new cultivar, showing the colors as true as it is reasonably possible to obtain in colored reproductions of this type.

The photograph on sheet 1 comprises a top perspective view of a typical potted plant of Delila.

The photograph at the top of sheet 2 is a comparison top perspective view showing Dallas Jewel (left) and Delila (right). In this comparison photograph, the depicted colors are not precise, but the differences in plant shape, growth habit, plant height and plant width are visible.

The photograph at the bottom of sheet 2 is a comparison view of fronds of Delila (top) and Dallas Jewel (bottom). In this comparison photograph, the depicted colors are not precise, but the differences in frond length, rachis length, quantity of pinnae, pinnae width, pinnae margin, number of lobes and pinnae aspect are visible.

In the following description, color references are made to The Royal Horticultural Society Colour Chart except where general terms of ordinary dictionary significance are used. Measurements and numerical values represent averages for six typical plants.

Botanical classification: *Neophrolepis exaltata* cultivar Delila.

Parentage: Naturally occurring sport or mutation of *Neophrolepis exaltata* cultivar Welch.

Propagation: By tissue culture.

Rooting habit: Fibrous and aggressive. Tissue culture plantlets develop roots within 7 days under warm (80° F.) conditions.

PLANT DESCRIPTION

A. Plant shape: Symmetrical and spherical in shape. Fronds of mature plants cover the entire container. Appropriate for hanging basket containers.

B. Growth habit: Arching to pendent.

C. Plant height: 18 cm from soil line to top of plant plane.

D. Plant width: 45 cm in diameter.

E. Plant vigor: Moderate.

F. Frond description:

1. *Leaf arrangement.*—one-pinnate.
2. *Frond length.*—22 cm.
3. *Frond width.*—5.5 cm.
4. *Rachis length.*—16 cm.
5. *Quantity of fronds.*—Numerous.

G. Pinnae description:

1. *Pinnae length.*—23 mm.
2. *Pinnae width.*—9 mm.
3. *Quantity of pinnae.*—29 per frond.
4. *Margin.*—Deeply crenate.
5. *Number of lobes.*—23.
6. *Pinnae base.*—Truncate.
7. *Pinnae aspect.*—Slightly curved inward towards midvein, undulated from pinnae base to tip giving a wavy, not flat, appearance.
8. *Pinnae attachment.*—Sessile.
9. *Pinnae texture.*—Shiny, smooth.
10. *Pinnae color.*—a. Immature, top side: 144A. b. Immature, under side: 144A. c. Intermediate, top side: 143A. d. Intermediate, under side: 143A. e. Mature, top side: 137A. f. Mature, under side: More green than 146A.
11. *Venation pattern.*—Pinnate.

Disease resistance: No resistance nor susceptibility to pathogens has been noted.

Spore formation: The new cultivar has not been observed to form spores.

CHART A

| CHARACTERISTIC | DALLAS JEWEL | DELILA |
|---|---|---|
| PLANT SHAPE | Upright and loose, nonsymmetrical | Symmetrical and spherical |
| GROWTH HABIT | Erect to slightly arching | Arching to pendent |
| PLANT HEIGHT | 30 cm from soil line to top of plant plane | 18 cm from soil line to top of plant plane |
| PLANT WIDTH | 36 cm diameter | 45 cm diameter |
| VIGOR | Moderate | Moderate |
| APPROPRIATE CONTAINER(S) | Appropriate for pots, too upright for hanging basket containers | Appropriate for hanging basket containers |
| LEAF ARRANGEMENT | 1-pinnate | 1-pinnate |
| FROND LENGTH | 31 cm | 22 cm |
| FROND WIDTH | 5 cm | 5.5 cm |
| RACHIS LENGTH | 25 cm | 16 cm |
| QUANTITY OF FRONDS | Moderate, open form | Numerous, dense form |
| PINNAE LENGTH | 24 mm | 23 mm |
| PINNAE WIDTH | 5 mm | 9 mm |
| QUANTITY OF PINNAE | 46 per frond | 29 per frond |
| PINNAE MARGIN | Finely crenate | Deeply crenate |
| NUMBER OF LOBES | 33 per pinnae | 23 per pinnae |
| PINNAE BASE | Truncate | Truncate |
| PINNAE ASPECT | Flat or slightly curved inward towards midvein | Slightly curved inward towards midvein, undulated from base to tip giving a wavy, not flat, appearance |
| PINNAE ATTACHMENT | Sessile | Sessile |
| PINNAE TEXTURE | Shiny, smooth | Shiny, smooth |
| PINNAE COLOR, IMMATURE, TOP SIDE | 144A | 144A |
| PINNAE COLOR, IMMATURE, UNDER SIDE | 144A | 144A |
| PINNAE COLOR, INTERMEDIATE, TOP SIDE | 137A | 143A |
| PINNAE COLOR, INTERMEDIATE, UNDER SIDE | More green than 146A | 143A |
| PINNAE COLOR, MATURE, TOP SIDE | 137A | 137A |
| PINNAE COLOR, MATURE, UNDER SIDE | More green than 146A | More green than 146A |
| VENATION PATTERN | Pinnate | Pinnate |

I claim:

1. A new and distinct cultivar of Fern plant named Delila, as illustrated and described.

* * * * *

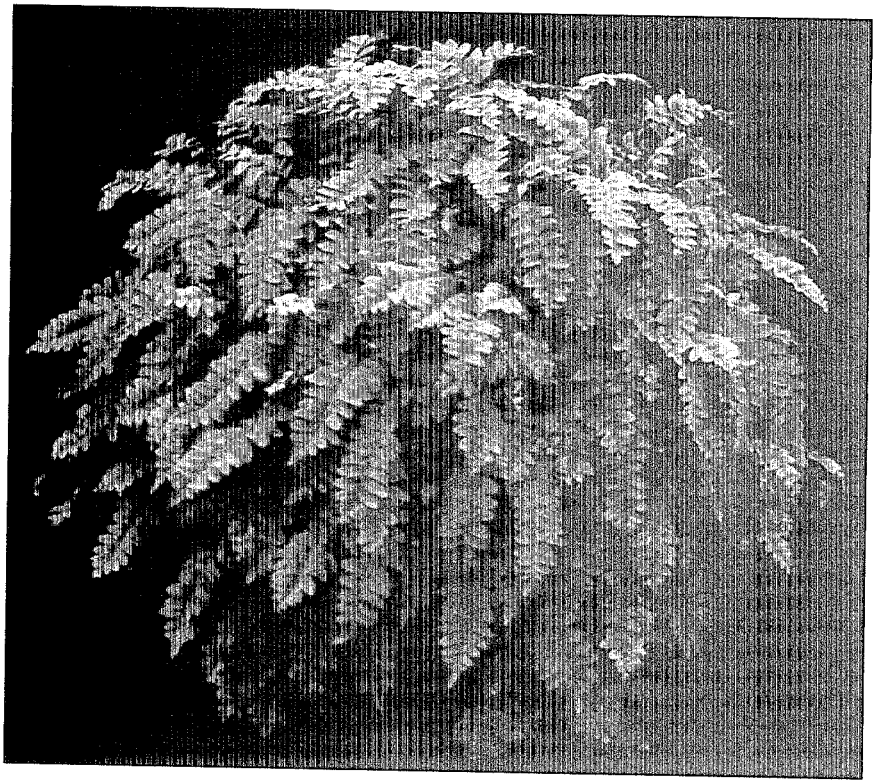

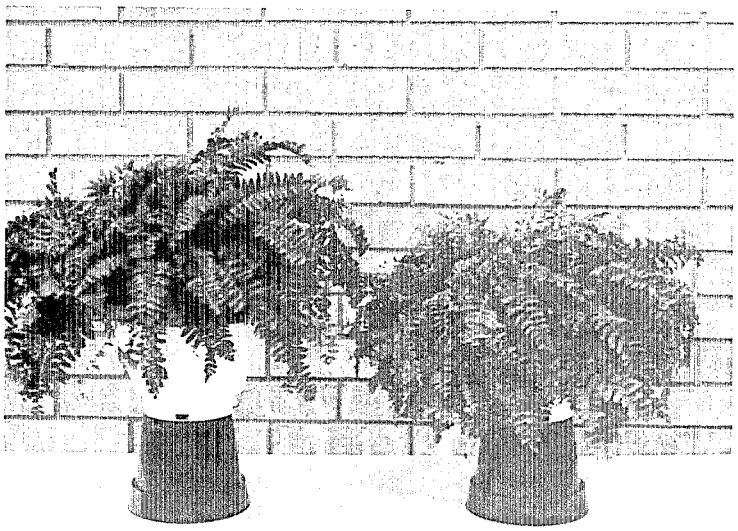
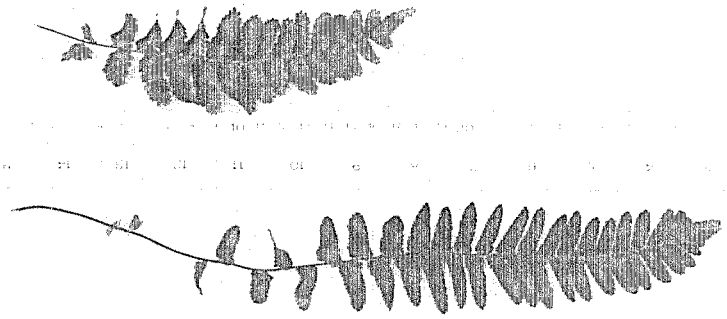

UNITED STATES PATENT AND TRADEMARK OFFICE

CERTIFICATE OF CORRECTION

PATENT NO. : Plant 9,260

DATED : August 22, 1995

INVENTOR(S) : Miriam Aharoni

It is certified that error appears in the above-indentified patent and that said Letters Patent is hereby corrected as shown below:

On the title page, item [54] and col. 1, line 1, change "Delila" to --Delilah--

In the Abstract, line 1, after "named", insert --Delilah, hereinafter--.

Signed and Sealed this

Twenty-first Day of May, 1996

*Attest:*

Bruce Lehman

BRUCE LEHMAN

*Attesting Officer*

*Commissioner of Patents and Trademarks*